US007329288B2

(12) United States Patent
Sabelle et al.

(10) Patent No.: US 7,329,288 B2
(45) Date of Patent: Feb. 12, 2008

(54) N-HETEROARYL SECONDARY PARA-PHENYLENEDIAMINE, A DYE COMPOSITION COMPRISING SUCH A PARA-PHENYLENEDIAMINE, A PROCESS FOR PREPARING THIS COMPOSITION AND USE THEREOF

(75) Inventors: Stéphane Sabelle, Paris (FR); Eric Metais, St-leu-le-Foret (FR)

(73) Assignee: L'Oreal S.A., Paris (FR)

( * ) Notice: Subject to any disclaimer, the term of this patent is extended or adjusted under 35 U.S.C. 154(b) by 222 days.

(21) Appl. No.: 11/067,414

(22) Filed: Feb. 28, 2005

(65) Prior Publication Data

US 2006/0005323 A1    Jan. 12, 2006

Related U.S. Application Data

(60) Provisional application No. 60/568,264, filed on May 6, 2004.

(30) Foreign Application Priority Data

Feb. 27, 2004  (FR) ................... 04 02025

(51) Int. Cl.
*A61K 7/13* (2006.01)
(52) U.S. Cl. ................ 8/405; 8/406; 8/407; 8/408; 8/409; 8/410; 8/411; 8/412; 8/414; 8/421; 544/3; 544/63; 546/249; 548/146; 548/215
(58) Field of Classification Search ............. 8/405, 8/406, 407, 408, 409, 410, 411, 412, 414, 8/421; 544/3, 63, 249, 146, 215
See application file for complete search history.

(56) References Cited

U.S. PATENT DOCUMENTS

| 3,192,225 | A | * | 6/1965 | Dexter et al. ............. 548/161 |
| 3,624,096 | A | | 11/1971 | Abramovitch et al. |
| RE30,199 | E | | 1/1980 | Rose et al. |
| 4,639,531 | A | * | 1/1987 | Baumann et al. .......... 549/261 |
| 4,823,985 | A | | 4/1989 | Grollier et al. |
| 5,061,289 | A | | 10/1991 | Clausen et al. |
| 5,180,399 | A | | 1/1993 | Grollier et al. |
| 5,380,340 | A | | 1/1995 | Neunhoeffer et al. |
| 5,534,267 | A | | 7/1996 | Neunhoeffer et al. |
| 5,624,937 | A | | 4/1997 | Reel et al. |
| 5,663,366 | A | | 9/1997 | Neunhoeffer et al. |
| 5,708,151 | A | | 1/1998 | Möckli |
| 5,766,576 | A | | 6/1998 | Löwe et al. |
| 6,099,592 | A | | 8/2000 | Vidal et al. |
| 6,284,003 | B1 | | 9/2001 | Rose et al. |
| 6,645,258 | B2 | | 11/2003 | Vidal et al. |
| 6,730,789 | B1 | | 5/2004 | Birault et al. |
| 2003/0196280 | A1 | * | 10/2003 | Lim et al. ............. 8/405 |

FOREIGN PATENT DOCUMENTS

| DE | 23 59 399 A1 | 6/1975 |
|---|---|---|
| DE | 38 43 892 A1 | 6/1990 |
| DE | 41 33 957 A1 | 4/1993 |
| DE | 195 43 988 A1 | 5/1997 |
| DE | 202 04 129 U1 | 8/2002 |
| EP | 0 175 641 A1 | 3/1986 |
| EP | 0 178 035 A1 | 4/1986 |
| EP | 0 576 251 A1 | 12/1993 |
| EP | 0 675 122 A2 | 10/1995 |
| EP | 0 714 954 B1 | 6/1996 |
| EP | 0 770 375 B1 | 5/1997 |
| FR | 2 586 913 A1 | 3/1987 |
| FR | 2 733 749 A1 | 11/1996 |
| FR | 2 801 308 A1 | 5/2001 |
| GB | 984 012 | 2/1965 |
| GB | 998 838 | 7/1965 |
| GB | 1 026 978 | 4/1966 |
| GB | 1153196 | 5/1969 |
| JP | 20-19576 | 1/1990 |
| JP | 05-163124 | 6/1993 |
| JP | 2526099 | 8/1996 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 97/20822 | 6/1997 |
| WO | WO 03/04018 A1 | 5/2003 |

OTHER PUBLICATIONS

STIC Search Report dated Mar. 27, 2007.*
Lieber et al., "Relative Acidities of 5-(Substituted Phenyl)amino-4phenyl-1,2,3-triazoles," Journal of Organic Chemistry, vol. 23, 1958, pp. 1916-1918.
Michael P. Sammes et al., "Synthetic Applications of N-N Linked heterocycles. Part 15. A Facile Synthesis of 4-Pyridyl-aryl)amines via the Reaction between 4-Chloro-1-pyridiniopyridinium Salts and Aryl Amines," Journal of the Chemical Society, Perkin Transactions 2, Chemical Society, Letchworth, GB, vol. 5, 1983, pp. 973-978.
T. Mitzuno et al., "Studies on the Conformational Isomers of 2-anilinopyridines and Related Compounds," Tetrahedron, vol. 27, No. 24, 1971, pp. 6011-6021.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The present disclosure relates to a novel family of N-heteroaryl secondary para-phenylenediamines, to their preparation, to their use for dyeing the hair and to a dye composition for dyeing keratin fibers, for example, human keratin fibers such as the hair, comprising, in a suitable dyeing medium, at least one heteroaryl secondary para-phenylenediamine. The disclosure also relates to the process using this composition, to its use and to the multi-compartment device and dyeing "kit".

28 Claims, No Drawings

OTHER PUBLICATIONS

English language Derwent Abstract of DE 202 04 129 A1, Aug. 29, 2002.
English Language Derwent Abstract for JP 2-19576 and JP 2526099 (Jan. 23, 1990 & Aug. 21, 1996).
English Language Derwent Abstract for EP 0770375 (May 2, 1997).
English Language Derwent Abstract for JP 05-163124 (Jun. 29, 1993).
Journal of Synthesis Organic Chemistry, Synthesis, "*High Pressure Organic Chemistry; XII. A Convenient Synthesis of Aromatic Amines from Activated Aromatic Flourides*," 1990 (12), pp. 1147-1148.

An International Journal for Rapid Communication of Synthetic Organic Chemistry, Synthetic Communications, "*Spiro-[4H-Pyrrolo[1,2-a][1,4]Benzodiazepine-4,4'-Piperidine] Derivatives As Potential Nootropic Agents: A Simple One-Pot Synthesis*," 1990, 20 (22), pp. 3537-3545.

French Search Report for FR 04 02025 (priority appliciation for U.S. Appl. No. 11/067,414, the present application) dated Aug. 26, 2004, Examiner De Jong.

* cited by examiner

N-HETEROARYL SECONDARY PARA-PHENYLENEDIAMINE, A DYE COMPOSITION COMPRISING SUCH A PARA-PHENYLENEDIAMINE, A PROCESS FOR PREPARING THIS COMPOSITION AND USE THEREOF

This application claims benefit of U.S. Provisional Application No. 60/568,264, filed May 6, 2004 and French Patent Application No. 0402025 filed Feb. 27, 2004 which are herein incorporated by reference.

The present disclosure relates to a novel family of N-heteroaryl secondary para-phenylenediamines, to their preparation and to their use in the oxidation dyeing of the keratin fibers.

It is known practice to dye keratin fibers, for example, human hair, with dye compositions comprising at least one oxidation dye precursor, including, for example, ortho- and para-phenylenediamines, ortho- and para-aminophenols, and heterocyclic compounds, which are generally referred to as oxidation bases. These oxidation bases, are colorless or weakly colored compounds which, when combined with oxidizing products, may give rise to colored compounds by a process of oxidative condensation.

It is also known that the shades obtained with these oxidation bases may be varied by combining them with couplers or coloration modifiers, the latter including, for example, aromatic meta-diaminobenzenes, meta-aminophenols, meta-diphenols and certain heterocyclic compounds such as indole compounds.

The variety of molecules used as oxidation bases and couplers makes it possible to obtain a wide range of colors.

The "permanent" coloration obtained by means of these oxidation dyes generally satisfies a certain number of requirements. It may have no toxicological drawbacks and it allows shades of the desired intensity to be obtained. It generally has good resistance to external agents such as light, bad weather, washing, permanent waving, perspiration and rubbing.

The dyes should also allow white hairs to be covered and, finally, they should be as unselective as possible, i.e. to allow the smallest possible differences in coloration to be produced over the entire length of the same keratin fiber, which is generally differently sensitized (i.e. damaged) between its end and its root.

The disclosure relates to a novel family of N-heteroaryl secondary para-phenylenediamines, capable of giving strong, aesthetic and sparingly selective colorations in varied shades, which show good resistance to the various attacking factors to which the fibers may be subjected. The present disclosure also relates to a process for preparing these N-heteroaryl secondary para-phenylenediamines and also to their use in the oxidation dyeing of the hair.

An embodiment of the disclosure is also novel compositions for dyeing keratin fibers, for example, human keratin fibers, such as the hair, comprising at least one N-heteroaryl secondary para-phenylenediamine.

The compositions of the present disclosure make it possible to obtain a very strong and sparingly selective coloration of keratin fibers, which is fast with respect to light, while at the same time avoiding the degradation of these fibers. In addition, these compositions have a good toxicological profile.

An embodiment of the disclosure is also the dyeing process using one or more composition according to the present disclosure for the dyeing of keratin fibers, for example, human keratin fibers, such as the hair, the use of the novel compositions and compounds and also a multi-compartment device and dyeing "kit".

Other characteristics, aspects, subjects and advantages of the present disclosure will emerge even more clearly on reading the description and the concrete, but non-limiting, examples that follow.

In the context of the present disclosure, the term "alkyl" means a linear or branched $C_1$-$C_{15}$ radical, which may, for example, be chosen from methyl, ethyl, n-propyl, isopropyl, and butyl. An alkoxy radical is a radical alk-O, the alkyl radical as defined above, for example methyloxy and ethyloxy. The term "halogen" may, for example, be chosen from Cl, Br, I and F.

The novel N-heteroaryl secondary para-phenylenediamines according to the present disclosure are compounds of formula (I):

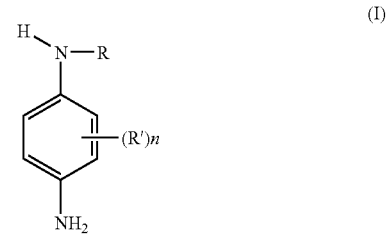

or the addition salts thereof, wherein:

R is chosen from pyrroles, pyrazoles, triazoles, oxazoles, isoxazoles, isothiazoles, imidazoles, pyridines, pyrimidines, pyrazines, pyridazines, quinolines, and thiophenes, each of which are optionally substituted with at least one radical chosen from alkyls, alkylcarbonyls, hydroxyls, alkoxys, alkylcarbonylaminos, monoalkylaminos and dialkylaminos;

R' is a hydrogen atom; and n is a number ranging from 1 to 4;

with the exception of the following compounds:

N-quinol-2-ylbenzene-1,4-diamine

N-(4-methylquinol-2-yl)benzene-1,4-diamine

N-quinol-4-ylbenzene-1,4-diamine

N-(4,6-dimethylpyrimidin-2-yl)-benzene-1,4-diamine 4-(2-pyridylamino)aniline

N-(4-pyridyl)-1,4-diaminobenzene.

R may, for example, be chosen from pyrazoles, pyridines, quinolines, acridines or thiophenes, each of which are optionally substituted with at least one radical chosen from methyl, t-butyl, phenyl, hydroxyl and alkoxy.

Compounds of formula (I) may, for example, be selected from:

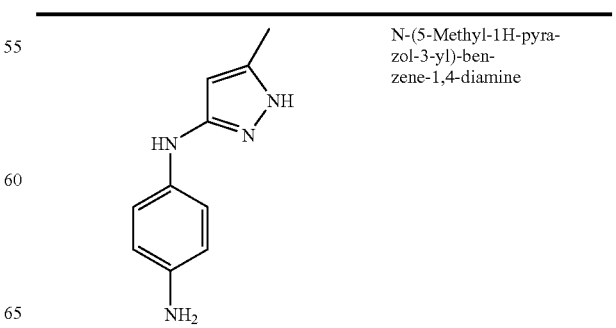

N-(5-Methyl-1H-pyrazol-3-yl)-benzene-1,4-diamine

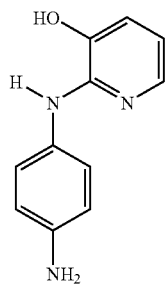 2-(4-Amino-phenyl-amino)-pyrid-3-ol

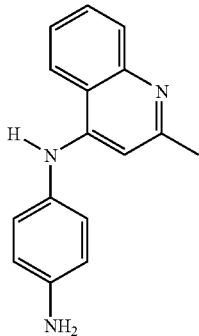 N-(2-Methyl-quinol-4-yl)-benzene-1,4-diamine

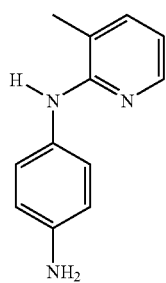 N-(3-Methyl-pyrid-2-yl)-benzene-1,4-diamine

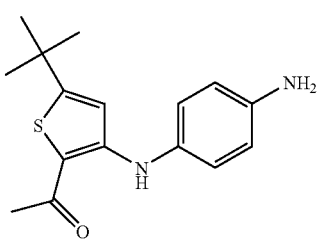 1-[3-(4-Amino-phenyl-amino)-5-tert-butyl-thiophen2-yl]ethanone

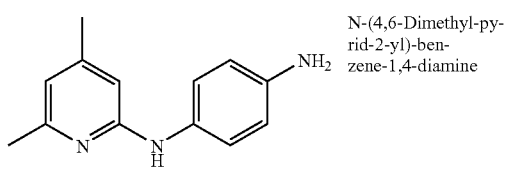 N-(4,6-Dimethyl-pyrid-2-yl)-benzene-1,4-diamine

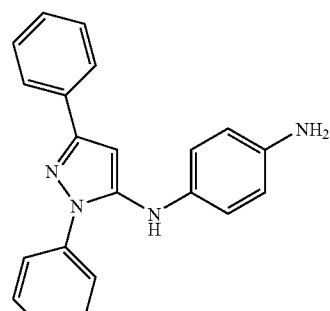 N-(2,5-Diphenyl2H-pyrazol-3-yl)-benzene-1,4-diamine

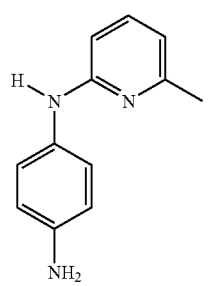 N-(6-Methyl-pyrid-2-yl)-benzene-1,4-diamine

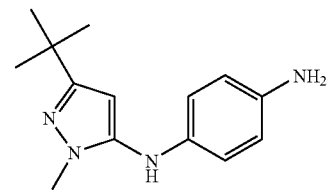 N-(5-tert-Butyl-2-methyl-2H-pyrazol-3-yl)-benzene-1,4-diamine

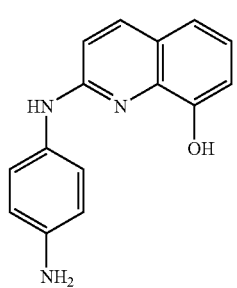 2-(4-Amino-phenyl-amino)-quinol-8-ol

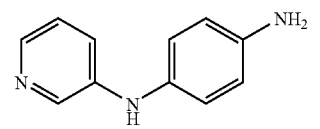 N-Pyrid-3-yl-benzene-1,4-diamine

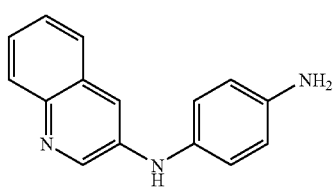 N-Quinol-3-yl-benzene-1,4-diamine

The addition salts of the oxidation bases and couplers that may be used in the context of the disclosure may be chosen from the addition salts with an acid, such as the hydrochlorides, hydrobromides, sulfates, citrates, succinates, tartrates, lactates, tosylates, benzenesulfonates, phosphates and acetates.

The compounds of formula (I) according to the present disclosure may be prepared according to a process comprising the following steps:

nucleophilic substitution of the halogen in the para position in the para-halonitrobenzene derivative with a primary amine of formula $RNH_2$ in the presence of a base (R is as defined above), and reduction of the nitro function of the compound obtained in the preceding step into an amine function, to obtain the compound of formula (I).

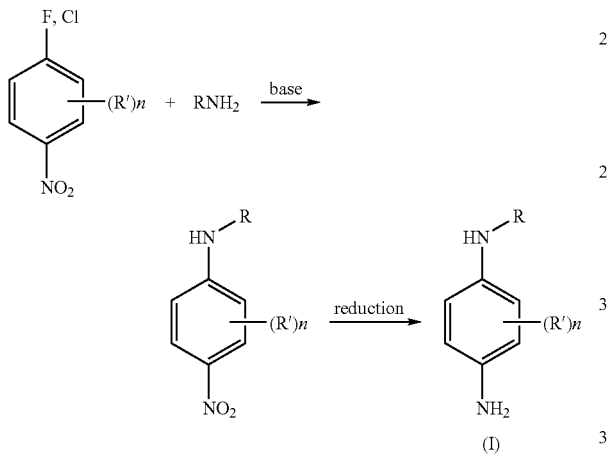

The first step of the synthesis is described in the reviews Synthesis 1990 (12), 1147-1148 and Synth. Commun. 1990, 20 (22), 3537-3545. The second step is a standard reduction step, for example by performing a hydrogenation reaction via heterogeneous catalysis in the presence of Pd/C, Pd(II)/C or Raney Ni, or alternatively by performing a reduction reaction with a metal, for example with zinc, iron, tin, etc. (Advanced Organic Chemistry, 4$^{th}$ edition, 1992, J. March, Wiley Interscience; Reduction in Organic Chemistry, M. Hudlicky, 1983, Ellis Honwood series Chemical Science).

The present disclosure also relates to the nitro compounds of formula (II):

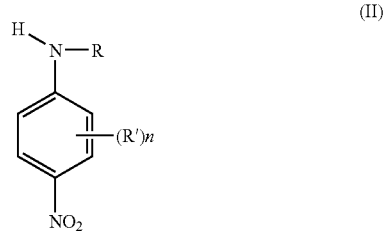

wherein:
R is chosen from pyrroles, pyrazoles, triazoles, oxazoles, isoxazoles, isothiazoles, imidazoles, pyridines, pyrimidines, pyrazines, pyridazines, triazines, quinolines and thiophenes each of which are optionally substituted with at least one radical chosen from alkylcarbonyls, hydroxyls, alkoxys, alkylcarbonylaminos, monoalkylaminos and dialkylaminos;

R' is a hydrogen atom; and n is a number ranging from 1 to 4;

with the exception of the following compounds:
4-pyridyl-p-nitrophenyleneamine; and
2-(4'-nitro)anilinopyridine.

Another embodiment is a process for preparing the N-heteroaryl secondary para-phenylenediamine compounds of formula (I) wherein the step of reduction of the corresponding nitro compound is performed, the corresponding nitro compound is the compound of the formula (I) wherein the amino group para to the group NHR is replaced with an nitro group.

The present disclosure also relates to the use of the compound of formula (I), as described above, for dyeing the hair.

The present disclosure also relates to a cosmetic composition for dyeing fibers, for example, human keratin fibers, such as hair, comprising, in a medium that is suitable for dyeing, at least one compound of formula (III):

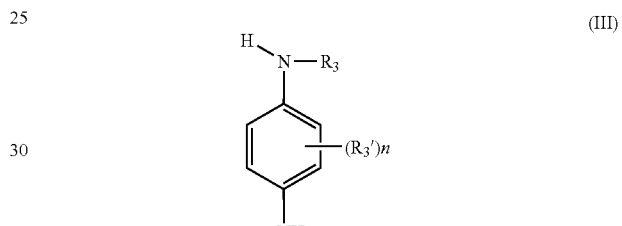

and the addition salts thereof, wherein:

$R_3$ is chosen from, for example, pyrroles, pyrazoles, triazoles, oxazoles, isoxazoles, thiazoles, isothiazoles, imidazoles, pyridines, pyrimidines, pyrazines, acridines, pyridazines, triazines, quinolines and thiophenes, each of which are optionally substituted with at least one radical chosen from alkyls, alkylcarbonyls, aryls, hydroxyls, alkoxys, alkylcarbonylaminos or monoalkylaminos and dialkylaminos, $R_3'$ is chosen from a hydrogen atom, a halogen atom, alkyls, alkoxys, hydroxyalkoxys, alkoxyalkyls, monohydroxyalkyls and polyhydroxyalkyls, n is a number ranging from 1 to 4.

$R_3$ of formula (III) may, for example, be chosen from a pyrazole, a pyridine and a quinoline.

The compound of formula (III) may, for example, be present in an amount ranging from 0.0001% to 20% and further, for example, from 0.005% to 6% by weight, relative to the total weight of the composition.

The medium that is suitable for dyeing may comprise water or a mixture of water and at least one organic solvent chosen from branched and unbranched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol; and aromatic alcohols, for instance benzyl alcohol or phenoxyethanol.

The solvents in the medium that is suitable for dyeing may, for example, be present in an amount ranging from 1% to 40% by weight, and further, for example, from 5% to 30% by weight, relative to the total weight of the dye composition.

The cosmetic composition as disclosed herein may also comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

The above at least one cosmetic adjuvant may be present in an amount ranging from 0.01% to 20% by weight, relative to the total weight of the composition.

A person skilled in the art will take care to select the at least one cosmetic adjuvant wherein the advantageous properties intrinsically associated with the oxidation dye composition as disclosed herein are not, or are not substantially, adversely affected by the at least one cosmetic adjuvant.

The composition of the present disclosure may, for example, comprise at least one oxidation coupler. Among the oxidation couplers that may, for example, be mentioned are meta-phenylenediamines, meta-aminophenols, meta-diphenols, naphthalene-based couplers and heterocyclic couplers, and the addition salts thereof.

The at least one oxidation coupler may, for example, be chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

For example, the concentration of the at least one oxidation coupler may range from 0.0001% to 20% by weight, by further example, from 0.005% to 6% by weight, relative to the total weight of the composition.

The composition of the present disclosure may, for example, comprise at least one additional oxidation base other than the compounds of formula (III).

The additional oxidation bases may be chosen, for example, from para-phenylenediamines, bis(phenyl)alkylenediamines, para-aminophenols, ortho-aminophenols and heterocyclic bases, and the addition salts thereof.

Among the para-phenylenediamines, further non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol, and the acid addition salts thereof.

The para-phenylenediamines mentioned above may further be chosen from para-phenylenediamine, para-tolylenediamine, 2-isopropyl-para-phenylenediamine, 2-α-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and the addition salts thereof.

Among the bis(phenyl)alkylenediamines, non-limiting mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetra-methylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Among the para-aminophenols, non-limiting mention may be made of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl]-2-methylphenol, bis(5'-amino-2'-hydroxy)phenylmethane and the acid addition salts thereof.

Among the ortho-aminophenols, non-limiting mention may be made of 2-aminophenol, 2-amino-5-methylphenol, 2-amino-6-methylphenol, 5-acetamido-2-amino-phenol, and the acid addition salts thereof.

Among the heterocyclic bases, non-limiting mention may be made of pyridine derivatives, pyrimidine derivatives and pyrazole derivatives.

Among the pyridine derivatives, non-limiting mention may be made of the compounds described, for example, in UK Patent Nos. GB 1 026 978 and GB 1 153 196, such as 2,5-diaminopyridine, 2-(4-methoxyphenyl)amino-3-aminopyridine, 3,4-diaminopyridine, and the acid addition salts thereof.

Other pyridine oxidation bases that may be useful in the present disclosure are the 3-aminopyrazolo[1,5-a]pyridine oxidation bases or the addition salts thereof described, for example, in French Patent Application No. FR 2 801 308. Non-limiting mention may be made of pyrazolo[1,5-a]pyrid-3-ylamine; 2-acetylaminopyrazolo-[1,5-a]pyrid-3-ylamine; 2-morpholin-4-ylpyrazolo[1,5-a]pyrid-3-ylamine; 3-aminopyrazolo-[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4- ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo-[1,5-a]pyrid-7-yl) (2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the acid addition salts thereof.

Among the pyrimidine derivatives, non-limiting mention may be made of the compounds described, for example, in German Patent No. DE 2 359 399; Japanese Patent Nos. JP 88-169 571 and JP 05 63 124; European Patent No. EP 0 770 375 or PCT Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, the addition salts thereof and the tautomeric forms thereof, when a tautomeric equilibrium exists.

Among the pyrazole derivatives, non-limiting mention may be made of the compounds described in German Patent Nos. DE 3 843 892 and DE 4 133 957; PCT Patent Application Nos. WO 94/08969 and WO 94/08970; French Patent Application No. FR-A-2,733,749; and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

The additional oxidation base may be present in an amount ranging from 0.0001% to 20%, for example, 0.005% to 6% by weight, relative to the total weight of the composition.

The addition salts of the oxidation bases and couplers that may be used in the context of the disclosure may be chosen, for example, from one or more addition salts with an acid such as the hydrochlorides, hydrobromides, sulfates, citrates, succinates, tartrates, lactates, tosylates, benzenesulfonates, phosphates and acetates.

The dye composition as disclosed herein may also comprise at least one direct dyes, which may be chosen from neutral, acidic or cationic nitrobenzene dyes, neutral, acidic or cationic azo direct dyes, neutral, acidic or cationic quinone, for example, anthraquinone direct dyes, azine direct dyes, triarylmethane direct dyes, indoamine direct dyes, and natural direct dyes. For example, the composition according to the disclosure comprises at least one dye chosen from cationic direct dyes and natural direct dyes.

Among the cationic direct dyes that may be used according to the disclosure, non-limiting mention may be made of the cationic azo direct dyes described in PCT Patent Application Nos. WO 95/15144 and WO 95/01772 and European Patent Application No. EP 714 954.

Among these cationic direct dyes, non-limiting mention may be made of the following dyes:

1,3-dimethyl-2-[[4-(dimethylamino)phenyl]azo]-1H-imidazolium chloride 1,3-dimethyl-2-[(4-aminophenyl)azo]-1H-imidazolium chloride 1-methyl-4-[(methylphenylhydrazono)methyl]pyridinium methyl sulfate.

Among the natural direct dyes that may be used according to the disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. It is also possible to use extracts or decoctions comprising natural dyes, for example, henna-based poultices or extracts.

The at least one direct dye may, for example, be present in an amount ranging from 0.001% to 20% by weight, and further, for example, from 0.005% to 10% by weight, relative to the total weight of the ready-to-use composition.

A ready-to-use dye composition is obtained by adding at least one oxidizing agent. The at least one oxidizing agent which may be used for the oxidation dyeing of keratin fibers may be chosen from, for example, hydrogen peroxide, urea peroxide, alkali metal bromates, persalts such as perborates and persulfates, peracids and oxidase enzymes, among which non-limiting mention may be made of peroxidases, two-electron oxidoreductases such as uricases, and four-electron oxygenases, for instance laccases. By further example, hydrogen peroxide may be used in the dye composition described above.

The pH of the dye composition disclosed herein ranges generally from 3 to 12, such as from 5 to 11. The pH may be adjusted to the desired value by adding at least one acidifying and/or at least one basifying agents usually used in the dyeing of keratin fibers, or alternatively using standard buffer systems.

Among the at least one acidifying agents that may be mentioned, examples include mineral or organic acids other than carboxylic diacids, for instance hydrochloric acid, orthophosphoric acid, sulfuric acid, carboxylic acids, for instance acetic acid, tartaric acid, citric acid and lactic acid, and sulfonic acids.

Among the at least one basifying agents that may be mentioned, examples include aqueous ammonia, alkali metal carbonates, alkanolamines such as monoethanolamine, diethanolamine and triethanolamine and also derivatives thereof, sodium hydroxide, potassium hydroxide and the compounds of formula:

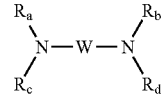

wherein W is a propylene residue optionally substituted with at least one hydroxyl group or a $C_1$-$C_4$ alkyl radical; $R_a$, $R_b$, $R_c$ and $R_d$, which may be identical or different, are each chosen from a hydrogen atom and $C_1$-$C_4$ alkyl and $C_1$-$C_4$ hydroxyalkyl radicals.

The cosmetic composition as disclosed herein may be in various forms, such as in the form of liquids, creams or gels, or in any other form that is suitable for dyeing keratin fibers, such as human hair.

Another embodiment of the present disclosure relates to a process wherein the composition according to the present disclosure as defined above is applied to the fibers and the colour is developed using an oxidizing agent. The colour may be developed at acidic, neutral or alkaline pH. The oxidizing agent may be added to the composition of the disclosure at the time of use. The composition according to the present disclosure may be used starting with an oxidizing composition comprising it, wherein the oxidizing composition is applied simultaneously with or sequentially to the composition disclosed herein.

In one embodiment, the composition disclosed herein is mixed, such as at the time of use, with a composition comprising, in a medium suitable for dyeing, at least one oxidizing agent, wherein the at least one oxidizing agent is present in an amount sufficient to develop a coloration. In this embodiment, a ready-to-use composition is provided, which is a mixture of a composition disclosed herein with at least one oxidizing agent chosen, for example, from hydrogen peroxide, urea peroxide, alkali metal bromates, persalts, peracids and oxidase enzymes. The mixture obtained, in the form of a ready-to-use composition, is then applied to the keratin fibers for a time that is sufficient to develop the desired coloration. After an action time of from 3 to 50 minutes such as from 5 to 30 minutes, the keratin fibers are rinsed, washed with a shampoo, rinsed again and then dried.

The oxidizing composition may also comprise various adjuvants conventionally used in hair dye compositions and as defined above.

The pH of the oxidizing composition comprising the oxidizing agent after mixing with the dye composition may range from 3 to 12, for example, from 5 to 11. It may be adjusted to the desired value by means of at least one acidifying and/or at leas tone basifying agent usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, for example, human hair.

The present disclosure also relates to the use of the cosmetic composition according to the disclosure comprising, in a medium that is suitable for dyeing, at least one compound of formula (III) for dyeing fibers, for example, keratin fibers such as the hair.

An embodiment of the disclosure is also a multi-compartment device or dyeing "kit", wherein a first compartment comprises the dye composition defined above and a second compartment comprises an oxidizing composition. This device may be equipped with a means for applying the desired mixture to the hair, such as the devices described in French Patent No. FR-2 586 913.

Using this device, it is possible to dye keratin fibers via a process that comprises mixing a dye composition as disclosed herein with an oxidizing agent as defined above, and applying the mixture obtained to the keratin fibers for a time that is sufficient to develop the desired coloration.

Other than in the operating examples, and where otherwise indicated, all numbers expressing quantities of ingredients, reaction conditions, and so forth used in the specification and claims are to be understood as modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The following examples are intended to illustrate the invention in a non-limiting manner.

EXAMPLES

Example 1

Synthesis of N-(5-methyl-1H-pyrazol-3-yl)benzene-1,4-diamine dihydrochloride (2)

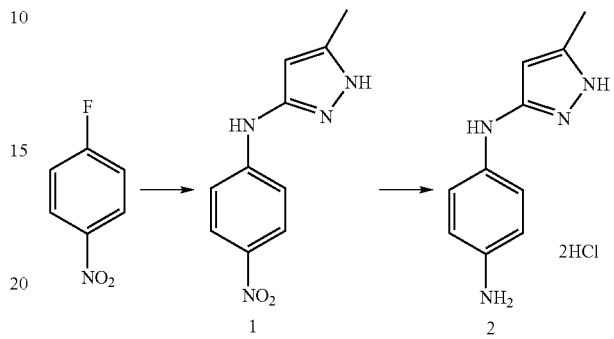

Step 1: Synthesis of 5-methyl-N-(4-nitrophenyl)-1H-pyrazol-3-amine (1)

0.3 g of 4-fluoronitrobenzene, 0.413 g of 3-amino-5-methylpyrazole, and 0.286 g of potassium tert-butoxide were added to a solution of 2.5 ml of THF. The reaction medium was heated at 60° C. for 7 hours and, after cooling to room temperature, was then poured into a water and ice mixture. The yellow precipitate formed was filtered off, reslurried in water and then dried over $P_2O_5$. 0.361 g of 5-methyl-N-(4-nitrophenyl)-1H-pyrazol-3-amine (1) was obtained.

Step 2: Synthesis of N-(5-methyl-1H-pyrazol-3-yl)benzene-1,4-diamine dihydrochloride The 5-methyl-N-(4-nitrophenyl)-1H-pyrazol-3-amine (1) obtained above was reduced with a boiling zinc/ammonium chloride/water/ethanol mixture. The corresponding amine was isolated in dihydrochloride form.

The NMR and mass spectra were in accordance with the expected structure of the product.

Example 2

Synthesis of 2-(4-aminophenylamino)pyridin-3-ol dihydrochloride (4)

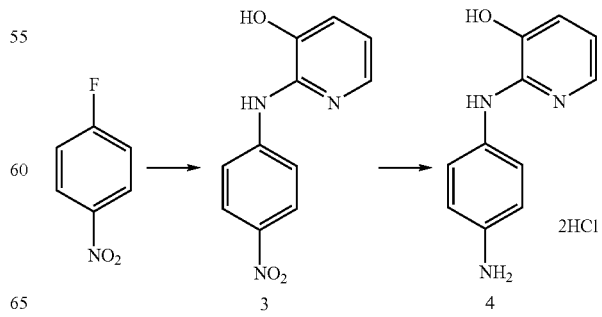

Step 1: Synthesis of 2-[(4-nitrophenyl)amino]pyridin-3-ol (3)

0.3 g of 4-fluoronitrobenzene, 0.468 g of 2-amino-3-hydroxypyridine, and 0.353 g of K$_2$CO$_3$ were added to a solution of 2.5 ml of N-methylpyrrolidinone. The reaction medium was heated at 60° C. for 1 hour and 0.286 g of potassium tert-butoxide was then added. Heating was then continued for 6 hours and, after cooling to room temperature, the reaction medium was poured into a water and ice mixture. The aqueous phase was extracted with ethyl acetate. The organic phase was dried over MgSO$_4$ and then evaporated to dryness under vacuum. 0.15 g of 2-[(4-nitrophenyl)amino]pyrid-3-ol (3) was obtained.

Step 2: Synthesis of 2-(4-aminophenylamino)pyrid-3-ol dihydrochloride (4)

The 2-[(4-nitrophenyl)amino]pyrid-3-ol (3) obtained above was reduced with a boiling zinc/ammonium chloride/water/ethanol mixture. The corresponding amine was isolated in dihydrochloride form.

The proton NMR and mass spectra were in accordance with the expected structure of the product.

Example 3

Synthesis of N-pyrid-2-ylbenzene-1,4-diamine dihydrochloride (6)

Step 1: Synthesis of N-(4-nitrophenyl)pyrid-2-amine (5)

0.3 g of 4-fluoronitrobenzene, 0.4 g of 2-aminopyridine, and 0.353 g of K$_2$CO$_3$ were added to a solution of 2.5 ml of N-methylpyrrolidinone. The reaction medium was heated at 60° C. for 1 hour and 0.286 g of potassium tert-butoxide was then added. Heating was then continued for 6 hours and, after cooling to room temperature, the reaction medium was then poured into a water and ice mixture. The yellow precipitate formed was filtered off, reslurried in water and then dried over P$_2$O$_5$. 0.09 g of N-(4-nitrophenyl)pyrid-2-amine (5) was obtained.

Step 2: Synthesis of N-pyrid-2-ylbenzene-1,4-diamine dihydrochloride (6)

The N-(4-nitrophenyl)pyrid-2-amine (5) obtained above was reduced with a boiling zinc/ammonium chloride/water/ethanol mixture. The corresponding amine was isolated in dihydrochloride form.

The proton NMR and mass spectra were in accordance with the expected structure of the product.

Example 4

Synthesis of N-(3-methylpyrid-2-yl)benzene-1,4-diamine dihydrochloride (8)

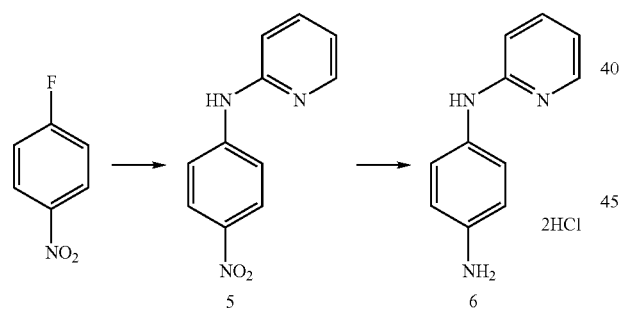

Step 1: Synthesis of 3-methyl-N-(4-nitrophenyl)pyrid-2-amine (7)

0.3 g of 4-fluoronitrobenzene, 0.46 g of 2-amino-3-methylpyridine, and 0.353 g of K$_2$CO$_3$ were added to a solution of 2.5 ml of N-methylpyrrolidinone. The reaction medium was heated at 60° C. for 1 hour and 0.286 g of potassium tert-butoxide was then added. Heating was then continued for 6 hours and, after cooling to room temperature, the reaction medium was then poured into a water and ice mixture. The yellow precipitate formed was filtered off, reslurried in water and then dried over P$_2$O$_5$. 0.18 g of 3-methyl-N-(4-nitrophenyl)pyrid-2-amine (7) was obtained.

Step 2: Synthesis of N-(3-methylpyrid-2-yl)benzene-1,4-diamine dihydrochloride (8)

The 3-methyl-N-(4-nitrophenyl)pyrid-2-amine (7) obtained above was reduced with a boiling zinc/ammonium chloride/water/ethanol mixture. The corresponding amine was isolated in dihydrochloride form.

The proton NMR and mass spectra were in accordance with the expected structure of the product.

Example 5

Synthesis of N-(6-methylpyrid-2-yl)benzene-1,4-diamine dihydrochloride (10)

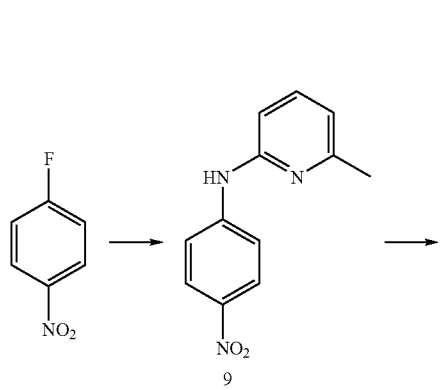

Example 6

Synthesis of 2-(4-aminophenylamino)quinol-8-ol dihydrochloride (12)

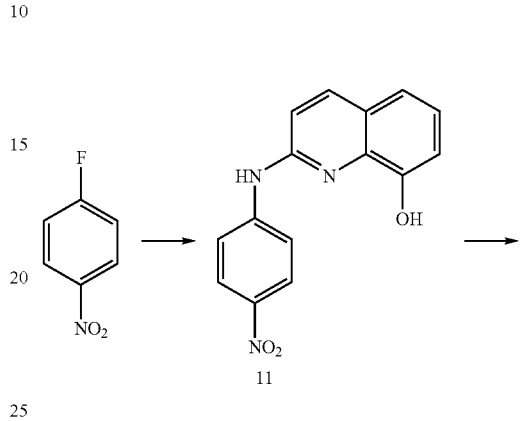

Step 1: Synthesis of 6-methyl-N-(4-nitrophenyl)pyrid-2-amine (9)

0.3 g of 4-fluoronitrobenzene, 0.46 g of 2-amino-3-methylpyridine, and 0.353 g of $K_2CO_3$ were added to a solution of 2.5 ml of N-methylpyrrolidinone. The reaction medium was heated at 60° C. for 1 hour and 0.239 g of potassium tert-butoxide was then added. Heating was then continued for 6 hours and, after cooling to room temperature, the reaction medium was then poured into a water and ice mixture. The yellow precipitate formed was filtered off, reslurried in water and then dried over $P_2O_5$. 0.108 g of 6-methyl-N-(4-nitrophenyl)pyrid-2-amine (9) was obtained.

Step 2: Synthesis of N-(6-methylpyrid-2-yl)benzene-1,4-diamine dihydrochloride (10)

The 6-methyl-N-(4-nitrophenyl)pyrid-2-amine (9) obtained above was reduced with a boiling zinc/ammonium chloride/water/ethanol mixture. The corresponding amine was isolated in dihydrochloride form.

The proton NMR and mass spectra were in accordance with the expected structure of the product.

Step 1: Synthesis of 2-[(4-nitrophenyl)amino]quinol-8-ol (11)

0.3 g of 4-fluoronitrobenzene, 0.683 g of 2-amino-8-hydroxyquinoline, and 0.353 g of $K_2CO_3$ were added to a solution of 2.5 ml of N-methylpyrrolidinone. The reaction medium was heated at 60° C. for 7 hours and, after cooling to room temperature, was then poured into a water and ice mixture. The yellow precipitate formed was filtered off, reslurried in water and then dried over $P_2O_5$. 0.45 g of 2-[(4-nitrophenyl)amino]quinol-8-ol (11) was obtained.

Step 2: Synthesis 2-(4-aminophenylamino)quinol 8-ol dihydrochloride (12)

The 2-[(4-nitrophenyl)amino]quinol-8-ol (11) obtained above was reduced with a boiling zinc/ammonium chloride/water/ethanol mixture. The corresponding amine was isolated in dihydrochloride form.

The proton NMR and mass spectra were in accordance with the expected structure of the product.

Example 7

Synthesis of N-(2-methylquinol-4-yl)benzene-1,4-diamine dihydrochloride (14)

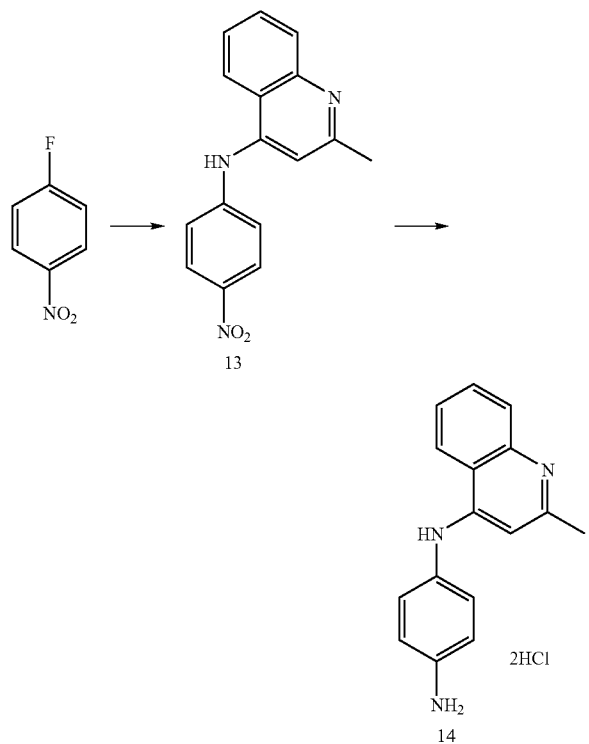

Step 1: Synthesis of 2-methyl-N-(4-nitrophenyl)quinol-4-amine (13)

0.6 g of 4-fluoronitrobenzene, 0.807 g of 4-aminoquinaldine, and 0.705 g of $K_2CO_3$ were added to a solution of 2.5 ml of N-methylpyrrolidinone. The reaction medium was heated at 60° C. for 6 hours and, after cooling to room temperature, was then poured into a water and ice mixture. The yellow precipitate formed was filtered off, reslurried in water and then dried over $P_2O_5$. 0.09 g of 2-methyl-N-(4-nitrophenyl)quinol-4-amine (13) was obtained after purification by chromatography on a column of silica (eluent: 50/50 dichloromethane/heptane).

Step 2: Synthesis of N-(2-methylquinol-4-yl)benzene-1,4-diamine dihydrochloride (14)

The 2-methyl-N-(4-nitrophenyl)quinol-4-amine (13) obtained above was reduced with a boiling zinc/ammonium chloride/water/ethanol mixture. The corresponding amine was isolated in dihydrochloride form.

The proton NMR and mass spectra were in accordance with the expected structure of the product.

Example 8

Dye Composition Using 2-(4-aminophenylamino)pyrid-3-ol Dihydrochloride (4) in Acidic Medium The following dye composition was prepared:

| Constituent | Amount |
| --- | --- |
| 2-(4-Aminophenylamino)pyrid-3-ol dihydrochloride (4) | $10^{-3}$ mol |
| 2-(2,4-Diaminophenoxy)ethanol hydrochloride | $10^{-3}$ mol |
| Dye support (1) | (*) |
| Demineralized water qs | 100 g |

(*): Dye support (1) pH 7:

| Constituent | Amount |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, the composition was mixed with an equal weight of 20-volume aqueous hydrogen peroxide solution (6% by weight). A final pH of 7 was obtained.

The mixture obtained was applied to locks of grey hair containing 90% white hairs. After an action time of 30 minutes, the locks were rinsed, washed with a standard shampoo, rinsed again and then dried.

The shade obtained was given in the table below:

| Shade observed | Yellow |
| --- | --- |

Example 9

Dye Composition Using 2-(4-aminophenylamino)pyrid-3-ol Dihydrochloride (4) in Basic Medium The following dye composition was prepared:

| Constituent | Amount |
| --- | --- |
| 2-(4-Aminophenylamino)pyrid-3-ol dihydrochloride (4) | $10^{-3}$ mol |
| 2-(2,4-Diaminophenoxy)ethanol hydrochloride | $10^{-3}$ mol |
| Dye support (2) | (*) |
| Demineralized water qs | 100 g |

(*): Dye support (2) pH 9.5

| Constituent | Amount |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, the composition was mixed with an equal weight of 20-volume aqueous hydrogen peroxide solution (6% by weight). A final pH of 9.5 was obtained.

The mixture obtained was applied to locks of grey hair containing 90% white hairs. After an action time of 30 minutes, the locks were rinsed, washed with a standard shampoo, rinsed again and then dried.

The shade obtained was given in the table below:

| Shade observed | orange |
|---|---|

Example 10

Dye Composition Using
N-pyrid-2-ylbenzene-1,4-diamine Dihydrochloride
(6) in Acidic Medium The following dye composition was prepared:

| Constituent | Amount |
|---|---|
| N-Pyrid-2-ylbenzene-1,4-diamine dihydrochloride (6) | $10^{-3}$ mol |
| 2-(2,4-Diaminophenoxy)ethanol hydrochloride | $10^{-3}$ mol |
| Dye support (1) | (*) |
| Demineralized water qs | 100 g |

(*): Dye support (1) pH 7

| Constituent | Amount |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, the composition was mixed with an equal weight of 20-volume aqueous hydrogen peroxide solution (6% by weight). A final pH of 7 was obtained.

The mixture obtained was applied to locks of grey hair containing 90% white hairs. After an action time of 30 minutes, the locks were rinsed, washed with a standard shampoo, rinsed again and then dried.

The shade obtained was given in the table below:

| Shade observed | yellow-brown |
|---|---|

Example 11

Dye Composition Using
N-pyrid-2-ylbenzene-1,4-diamine Dihydrochloride
(6) in Basic Medium The following dye composition was prepared:

| Constituent | Amount |
|---|---|
| N-Pyrid-2-ylbenzene-1,4-diamine dihydrochloride (6) | $10^{-3}$ mol |
| 2-(2,4-Diaminophenoxy)ethanol hydrochloride | $10^{-3}$ mol |
| Dye support (2) | (*) |
| Demineralized water qs | 100 g |

(*): Dye support (2) pH 9.5

| Constituent | Amount |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, the composition was mixed with an equal weight of 20-volume aqueous hydrogen peroxide solution (6% by weight). A final pH of 9.5 was obtained.

The mixture obtained was applied to locks of grey hair containing 90% white hairs. After an action time of 30 minutes, the locks were rinsed, washed with a standard shampoo, rinsed again and then dried.

The shade obtained was given in the table below:

| Shade observed | grey |
|---|---|

Example 12

Dye Composition Using
N-(6-methylpyrid-2-yl)benzene-1,4-diamine
Dihydrochloride (10) in Acidic Medium The following dye composition was prepared:

| Constituent | Amount |
|---|---|
| N-(6-Methylpyrid-2-yl)benzene-1,4-diamine dihydrochloride (10) | $10^{-3}$ mol |
| 2-(2,4-Diaminophenoxy)ethanol hydrochloride | $10^{-3}$ mol |
| Dye support (1) | (*) |
| Demineralized water qs | 100 g |

(*): Dye support (1) pH 7

| Constituent | Amount |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |

-continued

| Constituent | Amount |
| --- | --- |
| Polyethylene glycol containing 8 ethylene oxide units | 3.0 g |
| Na$_2$HPO$_4$ | 0.28 g |
| KH$_2$PO$_4$ | 0.46 g |

At the time of use, the composition was mixed with an equal weight of 20-volume aqueous hydrogen peroxide solution (6% by weight). A final pH of 7 was obtained.

The mixture obtained was applied to locks of grey hair containing 90% white hairs. After an action time of 30 minutes, the locks were rinsed, washed with a standard shampoo, rinsed again and then dried.

The shade obtained was given in the table below:

| Shade observed | yellow-brown |
| --- | --- |

Example 13-15

Dye Composition Using
N-(6-methylpyrid-2-yl)benzene-1,4-diamine
Dihydrochloride (10) in Basic Medium The following dye compositions were prepared:

| | Example | | |
| --- | --- | --- | --- |
| Constituent | 13 Amount | 14 Amount | 15 Amount |
| N-(6-Methylpyrid-2-yl)benzene-1,4-diamine dihydrochloride (10) | 10$^{-3}$ mol | 10$^{-3}$ mol | 10$^{-3}$ mol |
| 1H-Indol-6-ol | | 10$^{-3}$ mol | |
| 2-(2,4-Diaminophenoxy)ethanol hydrochloride | | | 10$^{-3}$ mol |
| 3-Amino-2-chloro-6-methylphenol hydrochloride | | | 10$^{-3}$ mol |
| Dye support (2) | (*) | (*) | (*) |
| Demineralized water qs | 100 g | 100 g | 100 g |

(*): Dye support (2) pH 9.5

| Constituent | Amount |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| C$_8$-C$_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

At the time of use, each composition was mixed with an equal weight of 20-volume aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

| | Example | | |
| --- | --- | --- | --- |
| | 13 | 14 | 15 |
| Shade observed | orange | grey | red-violet grey |

Example 16

Dye Composition Using
N-(3-methylpyrid-2-yl)benzene-1,4-diamine
Dihydrochloride (8) in Acidic Medium The following dye composition was prepared:

| Constituent | Amount |
| --- | --- |
| N-(3-Methylpyrid-2-yl)benzene-1,4-diamine dihydrochloride (8) | 10$^{-3}$ mol |
| 2-(2,4-Diaminophenoxy)ethanol hydrochloride | 10$^{-3}$ mol |
| Dye support (1) | (*) |
| Demineralized water qs | 100 g |

(*): Dye support (1) pH 7

| Constituent | Amount |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| C$_8$-C$_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| Na$_2$HPO$_4$ | 0.28 g |
| KH$_2$PO$_4$ | 0.46 g |

At the time of use, the composition was mixed with an equal weight of 20-volume aqueous hydrogen peroxide solution (6% by weight). A final pH of 7 was obtained.

The mixture obtained was applied to locks of grey hair containing 90% white hairs. After an action time of 30 minutes, the locks were rinsed, washed with a standard shampoo, rinsed again and then dried.

The shade obtained was given in the table below:

| Shade observed | yellow-brown |
| --- | --- |

Examples 17 and 18

Dye Composition Using
N-3-methylpyrid-2-yl)benzene-1,4-diamine
Dihydrochloride (8) in Basic Medium The following dye compositions were prepared:

|  | Example | |
|---|---|---|
| Constituent | 17 Amount | 18 Amount |
| N-(3-Methylpyrid-2-yl)benzene-1,4-diamine dihydrochloride (8) | $10^{-3}$ mol | $10^{-3}$ mol |
| 2-(2,4-Diaminophenoxy)ethanol hydrochloride | $10^{-3}$ mol | |
| 3-Amino-2-chloro-6-methylphenol hydrochloride | | $10^{-3}$ mol |
| Dye support (2) | (*) | (*) |
| Demineralized water qs | 100 g | 100 g |

(*): Dye support (2) pH 9.5

| Constituent | Amount |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volume aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

|  | Example | |
|---|---|---|
|  | 17 | 18 |
| Shade observed | grey | red-brown |

What is claimed is:

1. A compound of formula (I):

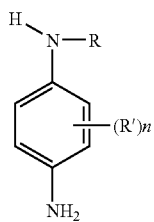

or the addition salts thereof, wherein:
R is chosen from pyrroles, pyrazoles, triazoles, oxazoles, isoxazoles, isothiazoles, imidazoles, pyridines, pyrimidines, pyrazines, pyridazines, quinolines, and thiophenes, each of which are optionally substituted with at least one radical chosen from alkyls, alkylcarbonyls, hydroxyls, alkoxys, alkylcarbonylaminos, monoalkylaminos and dialkylaminos;

R' is a hydrogen atom; and n is a number ranging from 1 to 4;

with the exception of the following compounds:
N-quinol-2-ylbenzene-1,4-diamine
N-(4-methylquinol-2-yl)benzene-1,4-diamine
N-quinol-4-ylbenzene-1,4-diamine
N-(4,6-dimethylpyrimidin-2-yl)-benzene-1,4-diamine
4-(2-pyridylamino)aniline
N-(4-pyridyl)-1,4-diaminobenzene.

2. A compound according to claim 1, wherein R is chosen from pyrazoles, pyridines and quinolines.

3. A compound according to claim 1, wherein R is substituted with a group chosen from methyl, t-butyl, phenyl, hydroxyl and alkoxy.

4. A compound according to claim 1, wherein the compound of formula (I) is chosen from N-(5-methyl-1H-pyrazol-3-yl)benzene-1,4-diamine, N-(6-methylpyrid-2-yl)benzene-1,4-diamine, N-(2-methylquinol-4-yl)benzene-1,4-diamine, N-(2,5-diphenyl-2H-pyrazol-3-yl)benzene-1,4-diamine, N-pyrid-3-ylbenzene-1,4-diamine, N-(4,6-dimethylpyrid-2-yl)benzene-1,4-diamine, N-Quinol-3-ylbenzene-1,4-diamine, 2-(4-aminophenylamino)pyrid-3-ol, N-(3-methylpyrid-2-yl)benzene-1,4-diamine, 2-(4-aminophenylamino)quinol-8-ol, 1-[3-(4-aminophenylamino)-5-tert-butylthiophen-2-yl]-ethanone, N-(5-tert-butyl-2-methyl-2H-pyrazol-3-yl)benzene-1,4-diamine, and the addition salts thereof.

5. A compound according to claim 1, wherein the addition salts are chosen from the hydrochlorides, hydrobromides, sulfates, citrates, succinates, tartrates, lactates, tosylates, benzenesulfonates, phosphates and acetates.

6. A compound of formula (II):

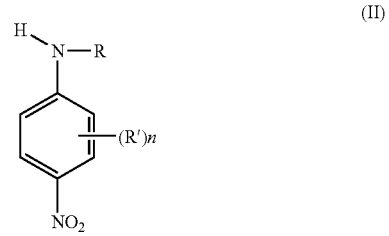

wherein:
R is chosen from pyrroles, pyrazoles, triazoles, oxazoles, isoxazoles, isothiazoles, imidazoles, pyridines, pyrimidines, pyrazines, pyridazines, triazines, quinolines and thiophenes each of which are optionally substituted with at least one radical chosen from alkyls, alkylcarbonyls, hydroxyls, alkoxys, alkylcarbonylaminos, monoalkylaminos and dialkylaminos;

R' is a hydrogen atom; and n is a number ranging from 1 to 4;

with the exception of the following compounds:
4-pyridyl-p-nitrophenyleneamine;
2-(4'-nitro)anilinopyridine; and
N-(4-nitrophenyl)pyrid-2-amine.

7. A process for preparing the compound of formula (I):

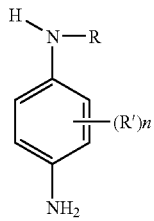

(I)

or the addition salts thereof, wherein:
R is chosen from pyrroles, pyrazoles, triazoles, oxazoles, isoxazoles, isothiazoles, imidazoles, pyridines, pyrimidines, pyrazines, pyridazines, quinolines and thiophenes, each of which are optionally substituted with at least one radical chosen from alkyls, alkylcarbonyls, hydroxyls, alkoxys, alkylcarbonylaminos, monoalkylaminos and dialkylaminos;
R' is a hydrogen atom; and
n is a number ranging from 1 to 4;
with the exception of the following compounds:
N-quinol-2-ylbenzene-1,4-diamine
N-(4-methylquinol-2-yl)benzene-1,4-diamine
N-quinol-4-ylbenzene-1,4-diamine
N-(4,6-dimethylpyrimidin-2-yl)-benzene-1,4-diamine
4-(2-pyridylamino)aniline
N-(4-pyridyl)-1,4-diaminobenzene
comprising reducing a nitro compound corresponding to the desired compound of formula (I).

8. A process for dyeing keratin fibers, comprising applying to the keratin fibers a composition comprising, in a medium suitable for dyeing, at least one compound of formula (I):

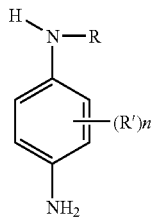

(I)

or the addition salts thereof, wherein:
R is chosen from pyrroles, pyrazoles, triazoles, oxazoles, isoxazoles, isothiazoles, imidazoles, pyridines, pyrimidines, pyrazines, pyridazines, quinolines and thiophenes, each of which are optionally substituted with at least one radical chosen from alkyls, alkylcarbonyls, hydroxyls, alkoxys, alkylcarbonylaminos, monoalkylaminos and dialkylaminos;
R' is a hydrogen atom; and
n is a number ranging from 1 to 4.

9. A cosmetic composition for dyeing fibers comprising, in a medium suitable for dyeing, at least one compound of formula (III):

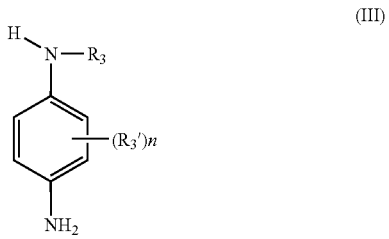

(III)

and the addition salts thereof, wherein:
$R_3$ is chosen from pyrroles, pyrazoles, triazoles, oxazoles, isoxazoles, thiazoles, isothiazoles, imidazoles, pyridines, pyrimidines, pyrazines, triazines, pyridazines, quinolines, thiophenes and acridines, each of which is optionally substituted with at least one radical chosen from alkyls, alkylcarbonyls, aryls, hydroxyls, alkoxys, alkylcarbonylaminos, monoalkylaminos and dialkylaminos;
$R_3'$ is chosen from a hydrogen atom, a halogen atom, alkyls, alkoxys, hydroxyalkoxys, alkoxyalkyls, monohydroxyalkyls and polyhydroxyalkyls; and
n is a number ranging from 1 to 4.

10. A composition according to claim 9, wherein the fibers are human keratin fibers.

11. A composition according to claim 9, wherein $R_3$ is chosen from pyrazoles, pyridines and quinolines.

12. A composition according to claim 9, wherein the compound of formula (III) is present in an amount ranging from 0.0001% to 20% by weight, relative to the total weight of the composition.

13. A composition according to claim 9, wherein the compound of formula (III) is present in an amount ranging from 0.005% to 6% by weight, relative to the total weight of the composition.

14. A composition according to claim 9, wherein the medium suitable for dyeing is chosen from water and a mixture of water and at least one organic solvent chosen from branched and unbranched $C_1$-$C_4$ lower alcohols, polyols, polyol ethers, and aromatic alcohols.

15. A composition according to claim 9, wherein the composition comprises at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

16. A composition according to claim 15, wherein the at least one cosmetic adjuvant is present in an amount ranging from 0.01% to 20% by weight, relative to the total weight of the composition.

17. A composition according to claim 9, wherein the composition comprises at least one coupler chosen from meta-phenylenediamines, meta-aminophenols, meta-diphenols, naphthalene-based couplers, heterocyclic couplers, and the addition salts thereof.

18. A composition according to claim 17, wherein the at least one coupler is present in an amount ranging from 0.0001% to 20% by weight, relative to the total weight of the composition.

19. A composition according to claim 9, wherein the composition comprises at least one additional oxidation base chosen from para-phenylenediamines, bis(phenyl)alkylenediamines, para-aminophenols, ortho-aminophenols, heterocyclic bases, and the addition salts thereof.

20. A composition according to claim 19, wherein the at least one additional oxidation base is present in an amount ranging from 0.0001% to 20% by weight, relative to the total weight of the composition.

21. A composition according to claim 9, wherein the composition comprises at least one dye chosen from cationic and natural direct dyes.

22. A process for dyeing keratin fibers comprising applying to said fibers, for a time that is sufficient to develop the desired coloration in the presence of an oxidizing agent, a cosmetic composition comprising, in a medium suitable for dyeing, at least one compound of formula (III):

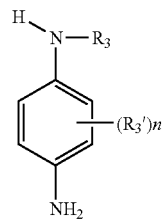

(III)

and the addition salts thereof, wherein:
$R_3$ is chosen from pyrroles, pyrazoles, triazoles, oxazoles, isoxazoles, thiazoles, isothiazoles, imidazoles, pyridines, pyrimidines, pyrazines, triazines, pyridazines, quinolines, thiophenes and acridines, each of which is optionally substituted with at least one radical chosen from alkyls, alkylcarbonyls, aryls, hydroxyls, alkoxys, alkylcarbonylaminos, monoalkylaminos and dialkylaminos;
$R_3'$ is chosen from a hydrogen atom, a halogen atom, alkyls, alkoxys, hydroxyalkoxys, alkoxyalkyls, monohydroxyalkyls and polyhydroxyalkyls; and
n is a number ranging from 1 to 4.

23. A process according to claim 22 wherein the keratin fibers are human keratin fibers.

24. A ready-to-use composition, comprising a cosmetic composition, in a medium suitable for dyeing, at least one compound of formula (III):

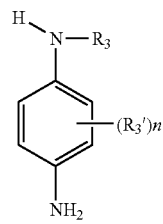

(III)

and the addition salts thereof, wherein:
$R_3$ is chosen from pyrroles, pyrazoles, triazoles, oxazoles, isoxazoles, thiazoles, isothiazoles, imidazoles, pyridines, pyrimidines, pyrazines, triazines, pyridazines, quinolines, thiophenes and acridines, each of which is optionally substituted with at least one radical chosen from alkyls, alkylcarbonyls, aryls, hydroxyls, alkoxys, alkylcarbonylaminos, monoalkylaminos and dialkylaminos;
$R_3'$ is chosen from a hydrogen atom, a halogen atom, alkyls, alkoxys, hydroxyalkoxys, alkoxyalkyls, monohydroxyalkyls and polyhydroxyalkyls; and
n is a number ranging from 1 to 4;

and at least one oxidizing agent chosen from hydrogen peroxide, urea peroxide, alkali metal bromates, persalts, peracids and oxidase enzymes.

25. A ready-to-use composition according to claim 24, wherein the at least one oxidizing agent is hydrogen peroxide.

26. A process for dyeing keratin fibers, comprising applying to the keratin fibers a composition comprising, in a medium suitable for dyeing, at least one compound of formula (III):

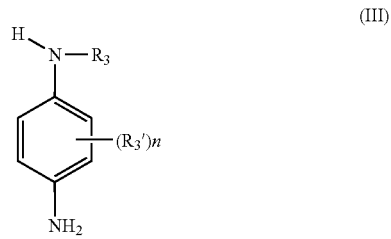

(III)

and the addition salts thereof, wherein:
$R_3$ is chosen from pyrroles, pyrazoles, triazoles, oxazoles, isoxazoles, thiazoles, isothiazoles, imidazoles, pyridines, pyrimidines, pyrazines, triazines, pyridazines, quinolines, thiophenes and acridines, each of which is optionally substituted with at least one radical chosen from alkyls, alkylcarbonyls, aryls, hydroxyls, alkoxys, alkylcarbonylaminos, monoalkylaminos and dialkylaminos;
$R_3'$ is chosen from a hydrogen atom, a halogen atom, alkyls, alkoxys, hydroxyalkoxys, alkoxyalkyls, monohydroxyalkyls and polyhydroxyalkyls; and
n is a number ranging from 1 to 4.

27. A process according to claim 26, wherein the keratin fibers are human keratin fibers.

28. A multi-compartment device, comprising
a first compartment comprising a cosmetic composition for dyeing keratin fibers, comprising, in a medium suitable for dyeing, at least one compound compound of formula (III):

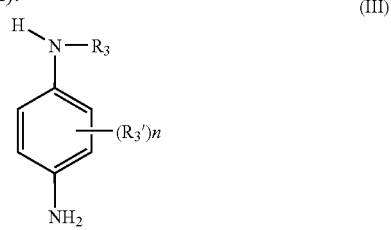

(III)

and the addition salts thereof, wherein:
$R_3$ is chosen from pyrroles, pyrazoles, triazoles, oxazoles, isoxazoles, thiazoles, isothiazoles, imidazoles, pyridines, pyrimidines, pyrazines, triazines, pyridazines, quinolines, thiophenes and acridines, each of which is optionally substituted with at least one radical chosen from alkyls, alkylcarbonyls, aryls, hydroxyls, alkoxys, alkylcarbonylaminos, monoalkylaminos and dialkylaminos;
$R_3'$ is chosen from a hydrogen atom, a halogen atom, alkyls, alkoxys, hydroxyalkoxys, alkoxyalkyls, monohydroxyalkyls and polyhydroxyalkyls; and
n is a number ranging from 1 to 4;
and a second compartment comprising at least one oxidizing agent.

* * * * *